United States Patent
Tang et al.

(10) Patent No.: US 8,822,716 B2
(45) Date of Patent: Sep. 2, 2014

(54) INTERMEDIATE OF CILASTATIN AND PREPARATION METHOD THEREOF

(75) Inventors: He Tang, Zhejiang (CN); Wenqiu Yuan, Zhejiang (CN); Jia Fu, Zhejiang (CN)

(73) Assignee: Zhejiang Hisoar Pharmaceutical Co., Ltd, Taizhou, Zhejiang (CN)

( * ) Notice: Subject to any disclaimer, the term of this patent is extended or adjusted under 35 U.S.C. 154(b) by 569 days.

(21) Appl. No.: 13/148,578

(22) PCT Filed: Feb. 8, 2010

(86) PCT No.: PCT/CN2010/070560
§ 371 (c)(1),
(2), (4) Date: Aug. 9, 2011

(87) PCT Pub. No.: WO2010/088862
PCT Pub. Date: Aug. 12, 2010

(65) Prior Publication Data
US 2011/0319653 A1    Dec. 29, 2011

(30) Foreign Application Priority Data
Feb. 9, 2009  (CN) .......................... 2009 1 0006259

(51) Int. Cl.
*C07C 69/716* (2006.01)
*C07C 69/67* (2006.01)
*C07C 59/115* (2006.01)
*C07C 51/08* (2006.01)
*C07C 253/00* (2006.01)
*C07C 69/675* (2006.01)
*C07C 67/08* (2006.01)
*C07C 67/313* (2006.01)
*C07C 319/14* (2006.01)

(52) U.S. Cl.
CPC ........... *C07C 69/675* (2013.01); *C07C 2101/02* (2013.01); *C07C 51/08* (2013.01); *C07C 253/00* (2013.01); *C07C 59/115* (2013.01); *C07C 67/08* (2013.01); *C07C 67/313* (2013.01); *C07C 319/14* (2013.01)
USPC ........... 560/174; 560/184; 562/585; 562/586

(58) Field of Classification Search
CPC .... C07C 69/716; C07C 69/67; C07C 69/675; C07C 59/115
USPC ........................... 560/174, 184; 562/585, 586
See application file for complete search history.

(56) References Cited

U.S. PATENT DOCUMENTS 4,346,099 A * 8/1982 Tanouchi et al. ............. 514/399

FOREIGN PATENT DOCUMENTS

| CN | EP0441371 A1 | 8/1991 |
|---|---|---|
| CN | 1587248 A | 3/2005 |
| CN | 101265187 A | 9/2008 |
| CN | 101475481 A | 7/2009 |

OTHER PUBLICATIONS

PCT International Search Report for PCT Application No. PCT/CN2010/070560 mailed on May 20, 2010.

* cited by examiner

*Primary Examiner* — Yevegeny Valenrod
(74) *Attorney, Agent, or Firm* — Lee & Hayes, PLLC

(57) ABSTRACT

Disclosed is a method for preparing 7-halo-2-oxoheptylate, an intermediate of cilastatin. The main steps are as follows: A. Addition reaction, in which 6-halo-hexanal is reacted with a cyanide to obtain 7-halo-α-hydroxyl-heptonitrile; B. Hydrolysis reaction, in which 7-halo-α-hydroxyl-heptonitrile is converted to 7-halo-α-hydroxyl-heptylic acid; C. Esterification reaction, in which 7-halo-α-hydroxyl-heptylic acid is converted to 7-halo-α-hydroxyl-heptylate; and D. Oxidation reaction, in which 7-halo-α-hydroxyl-heptylate is converted to 7-halo-2-oxoheptylate. 7-halo-α-hydroxyl-heptylic acid or ester thereof, which is a new intermediate for synthesizing 7-halo-2-oxoheptylate or cilastatin, and a method for synthesizing cilastatin are also disclosed. The methods of the invention are suitable for commercial production because of their simple process and mild reaction condition.

11 Claims, No Drawings

INTERMEDIATE OF CILASTATIN AND PREPARATION METHOD THEREOF

CROSS REFERENCE TO RELATED APPLICATIONS

This application is a 35 U.S.C. 371 national stage application of International Application No. PCT/CN2010/070560, filed Feb. 8, 2010, which claims priority to Chinese Application No. CN200910006259.6, filed Feb. 9, 2009, the entire contents of which are incorporated herein by reference.

FIELD OF THE INVENTION

The present invention relates to an intermediate of cilastatin, a method of preparation thereof, and a method for preparing cilastatin. In particular, the present invention relates to an alpha-hydroxyheptylic acid or an ester thereof and a preparation method for the same, a preparation method for 7-halo-2-oxoheptylate and a preparation method for cilastatin.

BACKGROUND OF INVENTION

Cilastatin is a renal dehydropeptidase inhibitor and its sodium salt is co-administered with imipenem for purpose of preventing renal metabolism of imipenem. The composition containing imipenem and cilastatin is used as a potent broad-spectrum antibacterial agent.

Cilastatin was first disclosed in U.S. Pat. No. 5,147,868, which was synthesized by multi-steps reactions including synthesis of ethyl 7-chloro-2-oxoheptylate by Gringnard reaction of 1-bromo-5-chloropentane with excessive diethyl oxalate. The method was improved by CHEN Xin-zhi et al in the Chinese patent application No. CN1587248A, but the total yield was only 24-43%, and the content of the resulting ethyl 7-chloro-2-oxoheptylate was merely 30-40%. Experiments showed that the content of the resulting product was only 30%, and it was difficult to be isolated and purified to obtain ethyl 7-chloro-2-oxoheptylate with high purity.

Methods for preparing ethyl 7-bromo-2-oxoheptylate by use of 1,5-dibromopentane, ethyl diethoxyacetate, propanedithiol, and so on as starting materials through reactions such as, cyclization, substitution, oxidization, etc. are disclosed in J. Med. Chem., 1987, 30 (6): 1074-1090 and Journal of Chinese Pharmaceuticals, 2005, 36(9), 531. However, these methods are not suitable for industrial production due to the expensive starting materials in these methods and the putrid propanedithiol.

PCT application WO98/15520 discloses a preparation method for obtaining ethyl 7-chloro-2-oxoheptylate with higher purity, in which 1-bromo-5-chloropentane and ethyl acetoacetate are used as starting materials, which are subjected to substitution reaction, then nitrosificated with nitroso-sulfuric acid, and deacetylated under acidic condition, and then reacted with formaldehyde to convert an oxime to a ketone, and finally refined by sodium bisulfite. However, expensive starting materials are still used in this method and large amount of waste acids are produced during nitrosification, which is not environment friendly.

Thus, a novel method of preparing an intermediate of cilastatin is still required in the field.

SUMMARY OF THE INVENTION

The first objective of the present invention is to provide a method for preparing an intermediate of cilastatin, 7-halo-2-oxoheptylate represented by Formula I,

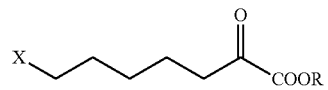

Formula I wherein X is halogen, such as, fluorine, chlorine, bromine or iodine, preferably bromine or chlorine; and R is C1-C4 hydrocarbyl, including saturated and unsaturated hydrocarbyl, such as, methyl, ethyl, n-propyl, iso-propyl, n-butyl, iso-butyl and the like, preferably ethyl group.

The second objective of the present invention is to provide a novel intermediate of cilastatin, 7-halo-α-hydroxyheptylic acid or an ester thereof represented by Formula II, for synthesis of 7-halo-2-oxoheptylate (i.e. the compound of Formula I) and further synthesis of cilastatin,

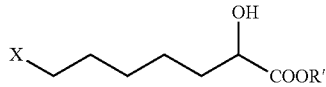

Formula II wherein X is halogen, such as, fluoro, chlorine, bromine or iodine, preferably bromine or chlorine; and R' is H or C1-C4 hydrocarbyl, including saturated and unsaturated hydrocarbyl, such as, methyl, ethyl, n-propyl, iso-propyl, n-butyl, iso-butyl, and the like, preferably ethyl group. The compound of Formula II is 7-halo-α-hydroxyl-heptylic acid provided R' is H. The compound of Formula II is 7-halo-α-hydroxyl-heptylate provided R' is C1-C4 hydrocarbyl.

The third objective of the invention is to provide a preparation method of cilastatin.

The present invention provides a method for preparing an intermediate of cilastatin, 7-halo-2-oxoheptylate represented by Formula I,

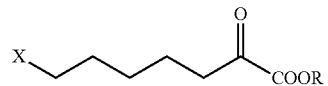

Formula I wherein X is halogen, such as, fluorine, chlorine, bromine or iodine, preferably bromine or chloro; and R is C1-C4 hydrocarbyl, including saturated and unsaturated hydrocarbyl, such as, methyl, ethyl, n-propyl, iso-propyl, n-butyl, iso-butyl, and the like, preferably ethyl group;

The method comprises the reaction steps as follows:

A. performing an addition reaction represented by the reaction scheme as follows, in which a cyanide is used to convert 6-halohexanal to 7-halo-α-hydroxyl-heptonitrile:

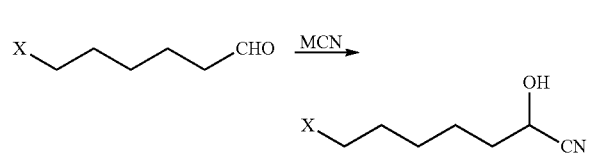

wherein the definition of X in the reaction scheme is the same as the above; M is an alkali metal, an alkaline earth metal or H; the alkali metal may be for example lithium, sodium or potassium, etc; the alkaline earth metal may be for example magnesium or calcium and etc; and wherein the addition reaction is an addition of an aldehyde with a cyanide to obtain α-hydroxynitrile;

B. performing a hydrolysis reaction represented by the reaction scheme as follows, in which 7-halo-α-hydroxyl-heptonitrile is converted to 7-halo-α-hydroxyl-heptylic acid:

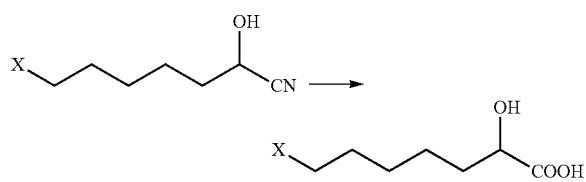

X in the reaction scheme has the same definition as the above, and in one embodiment, the hydrolysis reaction is an acid catalyzed hydrolysis of an α-hydroxynitrile to an α-hydroxy acid.

C. performing an esterification reaction represented by the reaction scheme as follows, in which 7-halo-α-hydroxyl-hepatenoic acid is converted to 7-halo-α-hydroxyl-heptylate:

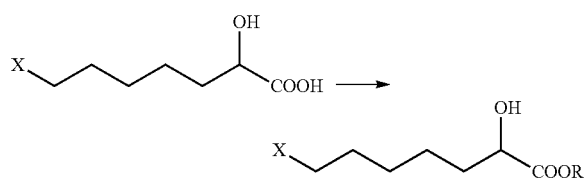

X and R in the reaction scheme have the same definitions respectively as the above.

in one embodiment, the esterification reaction is an acid catalyzed synthesis of an ester from an organic acid and an alcohol; and D. performing an oxidation reaction represented by the reaction scheme as follows, in which 7-halo-α-hydroxyl-heptylate is converted to 7-halo-2-oxoheptylate (the compound of Formula I):

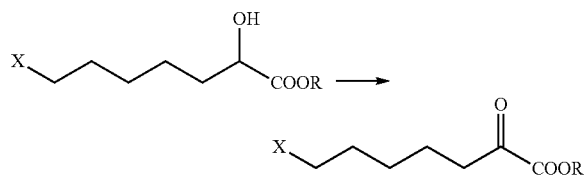

X and R in the reaction scheme have the same definitions respectively as the above. According to one embodiment of the present invention, in the above-described step A, the cyanide is selected from HCN, or $NaHSO_3$ and a metal cyanide (also known as $NaHSO_3$/metal cyanide, or "combination of $NaHSO_3$ and a metal cyanide", as well as other names appropriate in the art), in which the metal cyanide is an alkali metal or an alkaline earth metal cyanide, such as potassium cyanide, sodium cyanide, calcium cyanide, or a mixture of two or more of them, preferably KCN or NaCN. $NaHSO_3$ and a metal cyanide is used to replace HCN which has a low boiling point by treating the addition product resulting from 6-halo-hexanal and $NaHSO_3$ with the metal cyanide. Thus, the molar ratio of $NaHSO_3$ to the metal cyanide is typically about 1:1. The specific use of $NaHSO_3$ and a metal cyanide can be easily learned by those skilled in the art according to the prior art (e.g. as described in HUANG Xian, et al, "New Compilation of Organic Chemistry on Synthesis" Chemical Industry Press, p. 532), as well as in combination with the teaching herein. The solvent in the reaction is water. The resulting product is used in the next reaction after being stratified directly or extracted with an organic solvent and concentrated. The molar ratio of the cyanide to 6-halo-1-hexanal is 3:1-1:1, preferably 1.5:1-1:1, more preferably 1.2:1. The reaction temperature is from −10 to 40° C., preferably from 20 to 30° C.

According to one embodiment of the present invention, in the above-described step B, 7-halo-α-hydroxylheptonitrile is hydrolyzed with an inorganic acid presented to obtain 7-halo-α-hydroxyl-heptylic acid, and the inorganic acid may be sulfuric acid, hydrochloric acid or a mixture thereof, preferably concentrated hydrochloric acid, more preferably 34%-36% of hydrochloric acid. The solvent in the reaction is water. The molar ratio of the inorganic acid to 7-halo-α-hydroxylheptonitrile is 5:1-15:1, preferably 6:1-12:1, more preferably about 9:1. The reaction temperature is from 15 to 40° C., preferably from 20 to 40° C., more preferably from 28 to 32° C. The reaction time is 72-200 h, preferably 30-160 h.

According to one embodiment of the present invention, in the above-described step C, 7-halo-α-hydroxylheptylic acid and an alcohol are subjected to an esterification reaction to give 7-halo-α-hydroxyl-heptylate, in which the alcohol used is a C1-C4 alcohol, such as methanol, ethanol, isopropanol, and n-butanol, preferably ethanol. In one embodiment, the esterification reaction is acid catalyzed, in which the acid is an inorganic acid, such as, sulfuric acid, hydrochloric acid or a mixture of them, preferably sulfuric acid. The organic solvent may be the alcohol used as the reactant, or together with any additional inert organic solvent, such as, benzene, toluene, chloroform, dichloroethane, ethyl acetate, isopropyl acetate, butyl acetate, or a mixture of any two or more of them. The molar ratio of the alcohol to 7-halo-α-hydroxylheptylic acid is 5:1-50:1, preferably 7:1-25:1, further preferably 10:1-20:1, and more preferably about 15:1. The esterification reaction may perform under the condition of solvent reflux, upon which the reaction temperature is the temperature for the solvent reflux, and may also perform under other routine conditions, upon which the reaction temperature is from 50° C. to 100° C.

According to one embodiment of the invention, in the above-described step D, 7-halo-α-hydroxylheptylate is oxidized by an oxidizer to give 7-halo-2-oxoheptylate. The oxidizer used may be any of suitable oxidizers, the examples of which include $MnO_2$, $KMnO_4$, Jones Reagent, hypohalogenite, or a mixture of two or more of them. The hypohalogenite is preferably an alkali metal hypohalogenite, the examples of which includes NaOCl, NaOBr, KOCl, KOBr, or a mixture thereof, preferably Jones reagent or sodium hypochlorite. In one embodiment, when Jones Reagent is used as the oxidizer, the molar ratio of Jones Reagent to 7-halo-α-hydroxylheptylate is 0.7:1-1.0:1, preferably 0.8:1-0.9:1, more preferably about 0.83:1; and the reaction temperature is from −5 to 15° C., preferably from 0 to 10° C. In one embodiment, when hypohalogenite is used as the oxidizer, the pH of the reaction system was stabilized with a buffer to be 6-9, preferably 7-8. The buffer may be any suitable buffer which allows the reaction performing smoothly, but most preferably an inorganic buffer. The preferred inorganic buffer is sodium bicarbonate, potassium bicarbonate, $K_2HPO_4$/$KH_2PO_4$ or a mixture of two or more of them. 2,2,6,6-tetramethylpiperidinooxy (TEMPO) free radical or the like, such as 4-methoxy-2,2,6, 6-tetramethylpiperidinooxy free radical, and an alkali metal bromide serve as a co-catalyst. Example of the alkali metal bromide includes sodium bromide, potassium bromide, etc., preferably potassium bromide. The organic solvent used may be any of suitable organic solvents, the examples of which include ether, alkyl halide, alkane, aromatic hydrocarbon, or a mixture of two or more of them, preferably dichloromethane, chloroform, isopropyl ether or a mixture of two or more of them. The molar ratio of the hypohalogenite to 7-halo-α-hydroxylheptylate is 1:1-1.5:1, preferably 1:1-1.3:1, and more preferably about 1.2:1. The reaction temperature is from −20 to 40° C., preferably from −2 to 10° C. After adding the hypohalogenite, the reaction further performs 0.2-4 h, preferably 0.5-1.0 h.

In one embodiment, the obtained alcohol product is oxidized into a ketone by using Jones reagent as the oxidizer in the above-described step D. In another embodiment, the alcohol is oxidized into a ketone by using 2,2,6,6-tetramethylpiperidinooxy free radical or the like and an alkali metal bromide as the co-catalyst, and the hypohalogenite as the oxidizer.

The present application provides a compound of Formula II, i.e. 7-halo-α-hydroxylheptylic acid or an ester thereof:

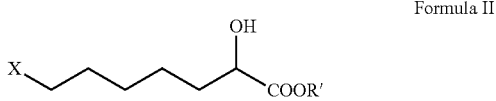

Formula II wherein X is halogen, such as, fluorine, chlorine, bromine or iodine, preferably bromine or chlorine; and R' is H or C1-C4 hydrocarbyl, including saturated and unsaturated hydrocarbyl, such as, methyl, ethyl, n-propyl, iso-propyl, n-butyl, iso-butyl and the like, preferably ethyl group. The compound of Formula II is a 7-halo-α-hydroxyl-heptylic acid provided R' is H; and the compound of Formula II is a 7-halo-α-hydroxyl-heptylate provided R' is C1-C4 hydrocarbyl.

The compound of Formula II may serve as an intermediate for synthesis of 7-halo-2-oxoheptylate or cilastatin, which is used to synthesize 7-halo-2-oxoheptylate (Formula I) and further cilastatin. The compound may be prepared following all or part of the steps described above, that is the compound of Formula II may be prepared subsequently through the steps A and B described above when R' is H, while the compound of Formula II may be prepared subsequently through the steps A, B, and C described above when R' is C1-C4 hydrocarbyl.

The present invention provides a use of a compound of Formula II as an intermediate in preparing 7-halo-2-oxoheptylate or cilastatin.

The present invention provides a method for preparing cilastatin. The said method comprises the following steps:

A) converting 6-halohexanal, 7-halo-α-hydroxynitrile, 7-halo-α-hydroxy acid, or 7-halo-α-hydroxycarboxylate to 7-halo-2-oxoheptylate according to the steps in the methods described above; and B) converting 7-halo-2-oxoheptylate to cilastatin, in which step B) is known. For example, as described in U.S. Pat. No. 5,147,868, ethyl 7-halo-2-oxoheptylate is condensed with s-2,2-dimethylcyclopropane-carboxamide under the catalysis of p-toluenesulfonic acid, and the resultant product is saponified and then reacted with L-cysteine hydrochloride to yield cilastatin.

The methods of the present invention are suitable for commercial production because of their simple processes and mild reaction conditions.

DETAILED DESCRIPTION OF THE INVENTION

It should be understood that in light of the disclosure herein, various modifications and improvements may be made by those skilled in the art to the present invention without departing from the spirit and scope of the present invention, all of which should be fallen within the claimed scope defined by the claims of the present application. Furthermore, it should be understood that the Examples provided herein is illustrative for the invention only, and is not to be construed as limiting the present invention in any way.

Example 1

Synthesis of 7-chloro-α-hydroxyheptonitrile 367 ml of water and 110 g (1.05 mol) of sodium bisulfite were added into a 1000 ml flask, and the mixture was cooled and stirred. 101 g (0.75 mol) of 6-chlorohexanal was dropped in at 5° C. within 40 min and the same temperature was maintained for additional 2 h. A solution of 51.5 g (1.05 mol) of sodium cyanide in 100 ml of water was dropped in at 5° C., and the mixture was further stirred at 20° C. for 12 h after dropping. The organic (upper) layer and the aqueous (lower) layer were separated. The aqueous layer was extracted with 100 ml of dichloromethane. The organic layers were combined and washed with water. The dichloromethane was recovered under normal pressure followed by reduced pressure, resulting in 113 g (0.7 mol) of a residue, i.e. 7-chloro-α-hydroxyheptonitrile, which may be used directly in the next reaction.

Example 2

Synthesis of 7-chloro-α-hydroxyheptonitrile 367 ml of water and 86.2 g (0.82 mol) of sodium bisulfite were added into a 1000 ml flask, and the mixture was cooled and stirred. 101 g (0.75 mol) of 6-chlorohexanal was dropped in at 30° C. within 40 min and the same temperature was maintained for additional 2 h. Then, a solution of 54 g (0.82 mol) of sodium cyanide in 100 ml of water was dropped in at 30° C., and the mixture was further stirred at 30° C. for 5 h after dropping. The organic (upper) layer and the aqueous (lower) layer were separated. The aqueous layer was extracted with 100 ml of dichloromethane. The organic layers were combined and washed with water. The dichloromethane was recovered under normal pressure followed by reduced pressure, resulting in 110 g (0.68 mol) of a residue, i.e. 7-chloro-α-hydroxyheptonitrile, which may be used directly in the next reaction.

Example 3

Synthesis of 7-chloro-α-hydroxyheptylic acid 113 g (0.7 mol) of 7-chloro-α-hydroxyheptonitrile was dropped in at 25° C. into a flask containing 733 ml of concentrated hydrochloric acid (35% in concentration of mass percentage, 8.0 mol). Agitation was performed at the same temperature for 140 h. The aqueous solution of sodium hydroxide was dropped in at the same temperature to adjust pH to 1.5. Then, filtration was performed and the filter cake was washed with 200 ml of toluene. The filtrates were combined and the organic layer was separated. 400 ml of water was introduced into the organic layer and the aqueous solution of sodium hydroxide was dropped in r to adjust pH of the aqueous layer to 7.5. The aqueous lower layer was separated and then washed again with toluene. The aqueous lower layer obtained was adjusted pH to 2 with concentrated hydrochloric acid and allowed to stand for isolation of the oily layer. The oily layer was heated with toluene to azeotropic point and dehydrated to dryness. Then, toluene was dried out to yield 82 g (0.45 mol) of 7-chloro-α-hydroxyheptylic acid which may be used directly in the next reaction. 10 g of the product was weighed and recrystallized in appropriate amount of pure benzene, resulting in 6 g of a white solid, mp: 70-72° C.

$^1$HNMR (CDCl$_3$) δ: 1.35-1.70 (m, 8H, CH$_2$), 3.60 (t, 2H, Cl—CH$_2$), 3.91 (t, 1H, CH), 5.08 (s, 1H, OH), 12.3 (s, 1H, COOH).

MS-ESI (m/z): 202.9[M+Na]$^+$.

Elemental analysis (C7H$_{13}$ClO$_3$), determined value (theoretical value, %): C46.8 (46.5), H7.29 (7.20).

IR: 3428 cm$^{-1}$ (OH), 1701 cm$^{-1}$ (—CO—).

Example 4

Synthesis of 7-chloro-α-hydroxyheptylic acid 113 g (0.7 mol) of 7-chloro-α-hydroxyheptonitrile was dropped in at 33-35° C. into a flask containing 450 ml of concentrated hydrochloric acid (35% in concentration of mass percentage, 4.9 mol), and agitated at the same temperature for 80 h. The aqueous solution of sodium hydroxide was dropped in at the same temperature to adjust pH to 1.5. Filtration was performed and the filter cake was washed with 200 ml of toluene. The filtrates were combined and the organic layer was separated. 400 ml water was introduced into the organic layer and the aqueous solution of sodium hydroxide was dropped in to adjust pH of the aqueous layer to 7.5. The aqueous lower layer was isolated and then washed again with toluene. The aqueous lower layer obtained was adjusted to pH to 2 with concentrated hydrochloric acid and allowed to stand for separation of the oily layer. The oily layer was heated with toluene to azeotropic point and dehydrated to dryness. Then, toluene was dried out to yield 72 g (0.40 mol) of 7-chloro-α-hydroxyheptylic acid which may be used directly in the next reaction.

Example 5

Synthesis of ethyl 7-chloro-α-hydroxyheptylate 80 g (0.44 mol) of 7-chloro-α-hydroxyheptylic acid and 400 ml (6.86 mol) of absolute ethanol were added into a 1000 ml flask. 30 g of concentrated sulfuric acid was dropped in. The reaction was heated at reflux until the starting materials disappeared as shown by gas chromatography (GC), followed by thorough recovering of ethanol under reduced pressure. The residue was decanted in batch into 300 ml of water containing 60 g of sodium bicarbonate. The mixture was extracted with (150+100) ml of dichloromethane. The organic layers were combined and washed with water. The dichloromethane was recovered thoroughly, resulting in 84 g (0.4 mol) of ethyl 7-chloro-α-hydroxyheptylate with 98% of chromatographic purity (GC).

$^1$HNMR (CDCl$_3$) δ: 1.22-1.25 (t, 3H, CH$_3$), 1.36-1.74 (m, 8H, CH$_2$), 3.00 (s, 1H, CH), 3.46-3.48 (t, 2H, Cl—CH$_2$), 4.11 (s, 1H, OH), 4.15-4.19 (m, 2H, C—CH$_2$).

MS-ESI (m/z): 230.9[M+Na]$^+$.

Elemental analysis (C7H$_{13}$ClO$_3$), determined value (theoretical value, %): C51.34 (51.75), H8.21 (8.15).

IR: 3469 cm$^{-1}$ (OH), 1732 cm$^{-1}$ (—CO—).

Example 6

Synthesis of ethyl 7-chloro-2-oxoheptylate 90 g (0.43 mol) of ethyl 7-chloro-α-hydroxyheptylate, 440 ml of dichloromethane, 6 g (0.05 mol) of potassium bromide, 1.0 g (0.006 mol) of TEMPO, and 660 ml of saturated solution of sodium bicarbonate cooled to internal temperature of −1 to 5° C. were added into a flask. The aqueous solution of 680 g of (0.45 mol) of sodium hypochlorite, which had be pre-cooled below 0° C., was added in batch into the flask and the temperature was maintained at 0° C. for 2.5 h after the feed was completed. The organic layer was separated. The aqueous layer was extracted once again with 100 ml of dichloromethane. The dichloromethane layer was washed firstly with 100 ml of 5% solution of sodium thiosulfate and then with 200 ml of water. After thorough recovering of the dichloromethane, the residue was distilled under reduced pressure and distillate cut at 90-92° C./2 mm Hg was collected, resulting in 77 g (0.37 mol) of ethyl 7-chloro-2-oxoheptylate with 95% of chromatographic purity (GC).

Example 7

Synthesis of ethyl 7-chloro-2-oxoheptylate 90 g (0.43 mol) of ethyl 7-chloro-α-hydroxyheptylate, 440 ml of dichloromethane, 6 g (0.05 mol) of potassium bromide, 1.0 g (0.006 mol) of TEMPO, and 660 ml of saturated solution of sodium bicarbonate cooled to internal temperature of −1° C. were added into a flask. The aqueous solution of 769 g (0.55 mol) of sodium hypochlorite, which had be pre-cooled below 0° C., was added in batch into the reaction flask and the temperature was maintained at 25° C. for 0.5 h after the added was completed. The organic layer was separated. The aqueous was extracted once again with 100 ml of dichloromethane. The dichloromethane layer was washed firstly with 100 ml of 5% solution of sodium thiosulfate and then with 200 ml of water. After thorough recovering of the dichloromethane, the residue was distilled under reduced pressure and distillate cut at 90-92° C./2 mm Hg was collected, resulting in 74 g (0.36 mol) of ethyl 7-chloro-2-oxoheptylate with 95% of chromatographic purity (GC).

Example 8

Synthesis of ethyl 7-chloro-2-oxoheptylate 30 g (0.144 mol) of ethyl 7-chloro-α-hydroxyheptylate was dissolved in 220 ml of acetone, and 77 g (0.12 mol) of Jones reagent was dropped in at 5° C. After the added was completed, the temperature was maintained for 8 h. Small amount of isopropanol was added to the mixture to remove the excessive Jones reagent. Filtration was performed and the filter bottle was washed with acetone. The filtrates were combined, concentrated, and extracted by adding 150 ml of water and 150 ml dichloromethane. The dichloromethane layer was washed once again with water and then concentrated to yield 27 g (0.13 mol) of ethyl 7-chloro-2-oxoheptylate with 93% of chromatographic purity (GC).

Reference Example

Synthesis of 6-chlorohexanal 136.5 g (1.0 mol) of 6-chloro-1-hexanol, 600 ml of dichloromethane, 12 g (0.1 mol) of potassium bromide, 1.6 g (0.0064 mol) of TEMPO, and 900 ml of saturated solution of sodium bicarbonate were added into a flask. The mixture was stirred, and cooled to 0° C. The aqueous solution of 1033 g (1.15 mol) of sodium hypochlorite, which had be pre-cooled to −5° C., was dropped quickly into the flask within 20 min while the internal temperature of the reactant being below 10°

C. The temperature was maintained at 10° C. for 0.5 h after the feed was completed. The organic layer was separated. The aqueous layer was extracted once again with 200 ml of dichloromethane. The organic layers were combined, washed one time with 200 ml of 5% solution of sodium thiosulfate, and then washed once again with 200 ml of water before thorough recovering of the dichloromethane. The residue was distilled under reduced pressure and distillate cut at 82-84° C./20 mm Hg was collected, resulting in 108 g of 6-chlorohexanal with 98% of chromatographic purity (GC).

The invention claimed is:

1. A method for preparing 7-halo-2-oxoheptylate represented by Formula I,

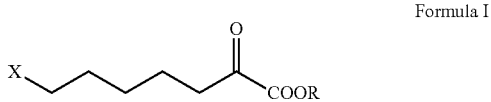

Formula I wherein X is halogen, and R is C1-C4 hydrocarbyl; and the method comprising the steps as follows:
A. performing an addition reaction, in which a cyanide is used to convert 6-halohexanal to a 7-halo-α-hydroxylheptonitrile;
B. performing a hydrolysis reaction, in which 7-halo-α-hydroxylheptonitrile is converted to 7-halo-α-hydroxylheptylic acid;
C. performing an esterification reaction, in which 7-halo-α-hydroxylheptylic acid is converted to 7-halo-α-hydroxylheptylate; and
D. performing an oxidation reaction, in which 7-halo-α-hydroxylheptylate is converted to 7-halo-2-oxoheptylate.

2. The method according to claim 1, wherein X is bromine or chlorine, and R is ethyl group.

3. The method according to claim 1, wherein in step A, the cyanide is selected from HCN, or NaHSO$_3$ and a metal cyanide, wherein the metal cyanide is selected from the group consisting of potassium cyanide, sodium cyanide, calcium cyanide, and a mixture of two or more of them; the molar ratio of the cyanide to 6-halohexanal is from 3:1 to 1:1; and the reaction temperature is from −10 to 40° C.

4. The method according to claim 1, wherein an acid is used in step B, and the acid is selected from the group consisting of sulfuric acid, hydrochloric acid and a mixture thereof; the molar ratio of the acid to 7-halo-α-hydroxyl-heptonitrile is from 5:1 to 15:1; the reaction temperature is from 15 to 40° C.; and the reaction time is from 72 to 200 h.

5. The method according to claim 1, wherein an C1-C4 alcohol is used in step C; the esterification reaction is an acid catalyzed reaction, and the acid is selected from the group consisting of sulfuric acid, hydrochloric acid and a mixture thereof; and the molar ratio of the alcohol to 7-halo-α-hydroxylheptylic acid is from 5:1 to 50:1.

6. The method according to claim 1, wherein an oxidizer is used in step D, which is selected from the group consisting of MnO$_2$, KMnO$_4$, Jones reagent, NaOCl, NaOBr, and a mixture of two or more of them.

7. The method according to claim 6, wherein the oxidizer used is Jones reagent.

8. The method according to claim 6, wherein in step D, the oxidizer used is NaOCl, NaOBr, or a mixture thereof; 2,2,6,6-tetramethylpiperidinooxy free radical or 4-methoxy-2,2,6,6-tetramethyl piperidinooxy free radical and a alkali metal bromide are used as a catalyst; the molar ratio of the oxidizer to 7-halo-α-hydroxylheptylate is from 1:1 to 1.5:1; the reaction temperature is from −20 to 40° C.; and the reaction time is from 0.2 to 4 h.

9. A method for preparing cilastatin, comprising the steps as follows:
A) converting 6-halo-hexanal, 7-halo-α-hydroxylheptonitrile, 7-halo-α-hydroxyl-heptylic acid, or 7-halo-α-hydroxylheptylate to 7-halo-2-oxoheptylate according to the steps in the method of any one of claims 1 to 7; and
B) converting 7-halo-2-oxoheptylate to cilastatin.

10. The method according to claim 5, wherein the C1-C4 alcohol that is used in step C is methanol or ethanol.

11. The method according to claim 4, wherein the acid used in step B is 34%-36% of hydrochloric acid.

* * * * *